United States Patent [19]

Luce et al.

[11] Patent Number: 5,587,748

[45] Date of Patent: Dec. 24, 1996

[54] JOYSTICK OVERRIDE CONTROL FOR AN OPHTHALMIC INSTRUMENT

[75] Inventors: David A. Luce, Clarence Center; Donald E. Miller, West Seneca, both of N.Y.

[73] Assignee: Leica Inc., Depew, N.Y.

[21] Appl. No.: 331,137

[22] Filed: Oct. 28, 1994

[51] Int. Cl.$^6$ .................................. A61B 3/14; A61B 3/10
[52] U.S. Cl. .......................... 351/208; 351/205; 351/209
[58] Field of Search ..................................... 351/208, 209, 351/210, 206, 205, 200

[56] References Cited

U.S. PATENT DOCUMENTS

| | | | |
|---|---|---|---|
| 4,881,807 | 11/1989 | Luce et al. | 351/208 |
| 5,337,095 | 8/1994 | Katsuragi et al. | 351/208 |

FOREIGN PATENT DOCUMENTS

4-50562  5/1992  Japan .

*Primary Examiner*—Hung Yuan Dang
*Attorney, Agent, or Firm*—Bean, Kauffman & Spencer

[57] ABSTRACT

An alignment override control for effecting automatic vertical alignment of a test axis of an ophthalmic instrument with the center of an eye is disclosed. The test axis is associated with optical alignment means of the instrument vertically movable by an elevation motor controlled by a motor drive. A joystick and a pair of directional switches are connected to the motor drive for manual positioning of the test axis. When the eye comes within a field of view defined by the optical means, the override control disconnects the switches and automatically signals the elevation motor to effect automatic alignment using signal information originating from the optical means.

9 Claims, 6 Drawing Sheets

JOYSTICK OVERRIDE CONTROL FOR AN OPHTHALMIC INSTRUMENT

BACKGROUND OF THE INVENTION

1. Field of the Invention

The present invention relates to alignment control systems for ophthalmic instruments, and more particularly to an automatic alignment control for overriding manual alignment means of an ophthalmic instrument.

2. Description of the Prior Art

Many ophthalmic instruments require alignment of a test axis with the center of a patient's eye and an element of the instrument to be spaced a chosen distance from the eye. One such instrument, the non-contact tonometer, has been used by practitioners in their ophthalmic practice for more than 20 years.

The early non-contact tonometers, manufactured by American Optical Corporation, used a joystick, a handle extending from a ball mounted to provide pivotal motion about the center of the ball, in order to move the instrument in a horizontal (X-Z) plane. To move the test axis horizontally in the X direction toward the center of the patient's eye, the joystick is tilted in a corresponding direction. To move the element in the Z direction toward or away from the eye, the joystick is tilted in a corresponding direction. Obviously, compound horizontal movement can be obtained by moving the joystick in a direction between the aforementioned orthogonal directions.

Vertical Y-axis motion in these earlier non-contact tonometers was provided by a separate knob linked by a belt to a threaded shaft mounted for rotation on the carrier and engaging a nut on the support to provide the vertical movement of the test axis. The "firing" button used to actuate the air puff of the early non-contact tonometers was located in the center of the knob used to control vertical, Y-axis, movement.

Later models of the non-contact tonometers produced by Reichert-Jung Ophthalmic Instruments (a successor to American Optical Corporation) and Tokyo Optical Company (Topcon) combined the vertical Y-axis control and "firing" button into the joystick. An example of this type of joystick is taught by Japanese Publication No. 4-50562. Such controls have several disadvantages as taught by the above-mentioned Japanese publication. One problem encountered resulted from twisting the wires used to connect the "firing" button to the instrument electronics and the expense associated with eliminating the twisted wire problem. Another disadvantage of rotating the joystick to control vertical motion was that the practitioner could not accomplish vertical motion when grasping the joystick in the conventional manner because the vertical motion frequently required one or more revolutions of the joystick in order to vertically position the test axis in the center of the eye. Also, many practitioners encounter difficulty in maintaining a horizontal location while adjusting the vertical location of the instrument.

One system for determining the position of a test axis in relation to the center of the eye, as well as the distance of an element from the eye, is taught in commonly owned U.S. Pat. No. 4,881,807. This patent discloses an optical alignment system having camera means and a visual display for indicating the relative position of the test axis when the eye is within a field of view of the optical alignment system, and teaches using a joystick for manually positioning the test axis or using three electric motors controlled by information obtained from the optical alignment system to automatically position the instrument.

SUMMARY OF THE INVENTION

An optical instrument includes a manually controlled ball-mounted lever, or joystick, for positioning optical means of the instrument, including a test axis and area detectors defining a field of view, relative to an eye of a patient. The optical means is fixed to a vertically movable support, which in turn is carried by a horizontally movable carrier. The joystick mechanically moves the carrier in a horizontal plane relative to a frame to center the test axis and space the optical means a proper distance from the eye.

The joystick is connected to a motor drive having an elevation motor for moving the support and optical means in either vertical direction. An actuator extends from the joystick and is arranged to alternately engage a pair of switches connected to the motor drive, such that activation of the elevation motor and its direction of rotation can be controlled with minimal rotational movement of the joystick about its longitudinal axis.

The motor drive is further connected to receive alignment signal information originating from the optical means, and a joystick override control is provided for disconnecting the joystick and automatically controlling the motor drive to vertically align the test axis with the center of the eye when the eye is within the field of view of the optical means.

Thus, in accordance with the present invention, a practitioner operates the joystick to manually position the test axis vertically until it is within the field of view, and then the joystick override control automatically signals the motor drive to complete vertical alignment of the test axis with the center of the eye.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION

Figure 1:
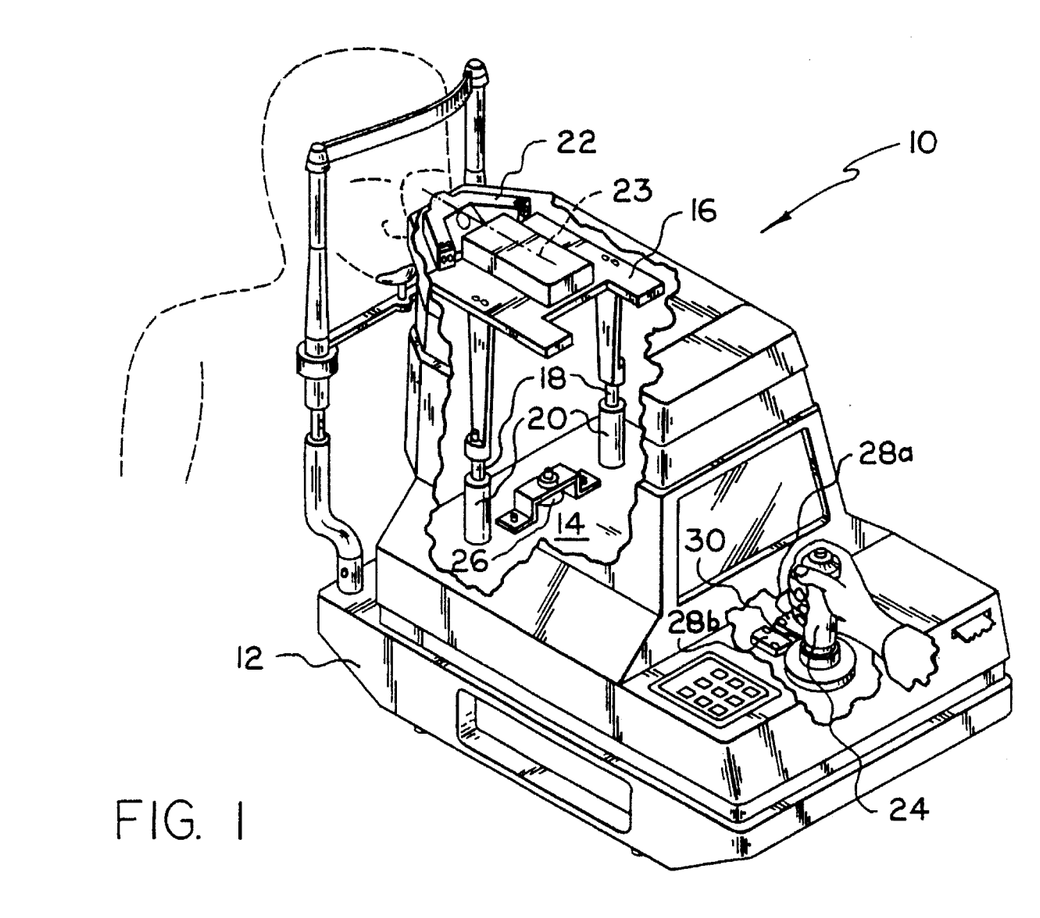
FIG. 1 is a perspective view of an improved ophthalmic instrument incorporating the present invention.

An improved ophthalmic instrument in the form of a non-contact tonometer (NCT) is shown in FIG. 1 and generally designated as 10. NCT 10 is conventional in that it includes a frame 12 having a horizontally movable carrier 14, a support 16 having shafts 18 slidably mounted by carrier tubes 20 for movement of the support vertically relative to carrier 14 and horizontally with the carrier, optical means 22 fixed to support 16 for testing an eye of a patient centered along a test axis 23 of the optical means, and a joystick 24 for controlling movement of optical means 22 in three dimensions. NCT 10 is preferably equipped with an optical alignment system of a type disclosed in commonly owned U.S. Pat. No. 4,881,807.

In accordance with the present invention, an elevation motor 26 is provided to automate upward and downward vertical motion of support 16 and optical means 22 in response to an up switch 28a and a down switch 28b alternately triggered by an actuator 30. Actuator 30 extends radially from joystick 24 and triggers switches 28a, 28b incident to minimal rotation of the joystick in either direction, thereby facilitating vertical positioning of test axis 23 relative to the eye.

Figure 2:
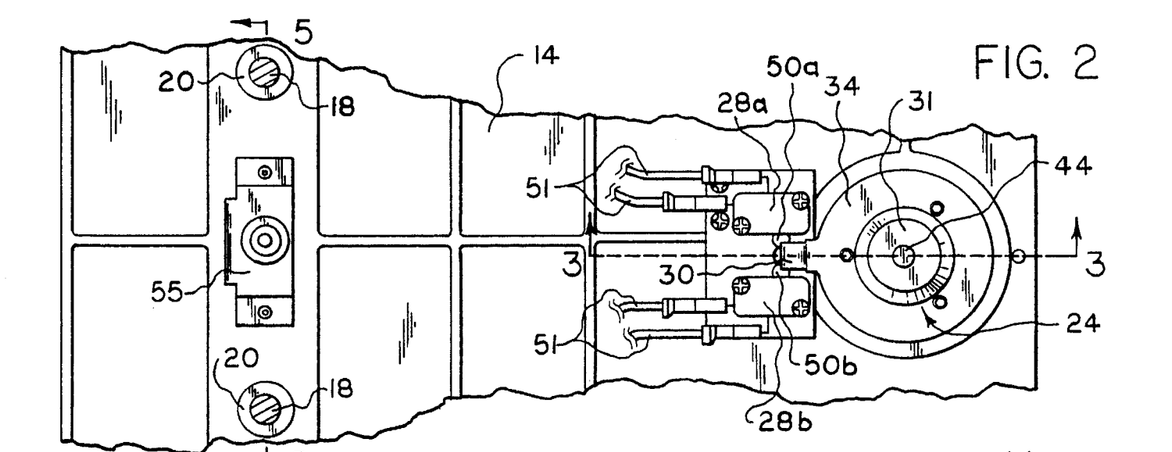
FIG. 2 is a top plan view of a joystick and switch means of the present invention.
Figure 3:
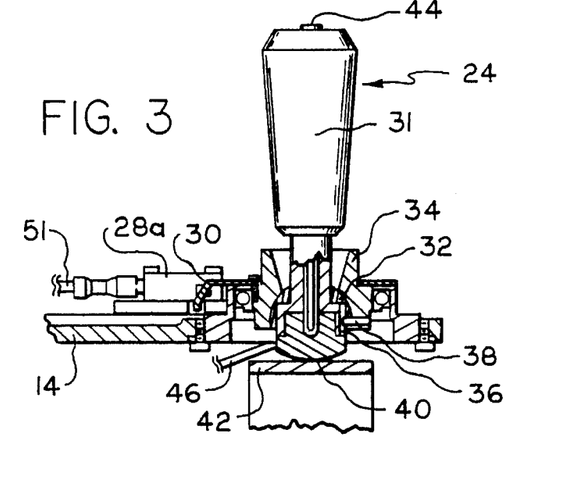
FIG. 3 is a sectional view taken generally along the line 3—3 in FIG. 2.
Figure 6:
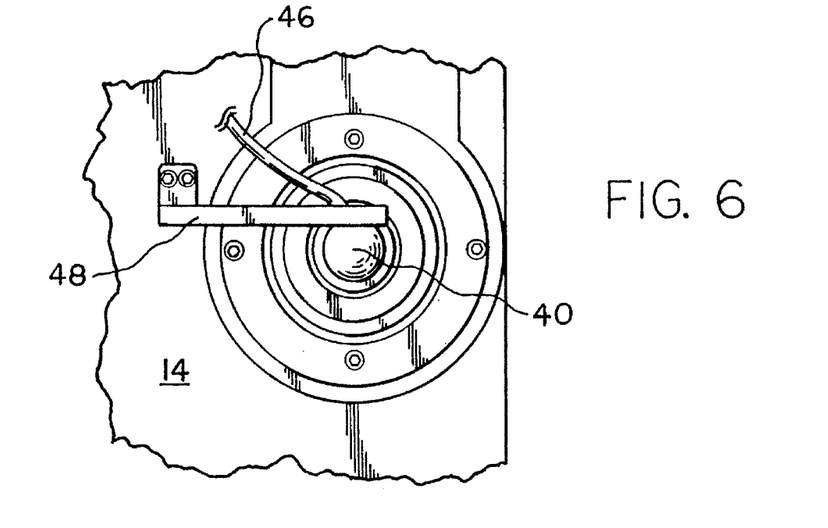
FIG. 6 is a bottom plan view of the joystick.

As best seen in FIGS. 2, 3, and 6, joystick 24 is generally conventional in structure except for actuator 30. Joystick 24 includes a handle portion 31 and is mounted in a known manner on carrier 14 by a teflon ball 32 received within a complementary socket 34 and having slot means 36 for accommodating a set screw 38 which permits coupled rotation of the joystick and socket about the longitudinal axis of the joystick in addition to tilting motion of the joystick within the socket. Joystick 24 also includes a rounded teflon foot 40 arranged to engage a smooth platform 42 fixed to frame 12 throughout the range of motion of carrier 14, and firing switch means 44 connected to a lead 46 for activating optical means 22. As depicted in FIG. 6 only, a retainer arm 48 is fixed to an underside of carrier 14 to underengage platform 42 incident to lifting motion exerted on joystick 24.

Actuator 30 is fixed to socket 34 to extend radially outward from joystick 24 between switches 28a, 28b in a reference rotational position, such that it operatively engages a switch bumper 50a to activate up switch 28a incident to slight rotation of joystick 24 in a clockwise direction and it operatively engages a switch bumper 50b to activate down switch 28b incident to slight rotation of joystick 24 in a counterclockwise direction. Switches 28a, 28b are preferably normally open switches of the general type known as "micro" switches. Obviously, other similar switches are possible.

Switches 28a, 28b are connected by leads 51 to motor control electronics, described in detail below, incorporating a joystick override control of the present invention.

Figure 4:
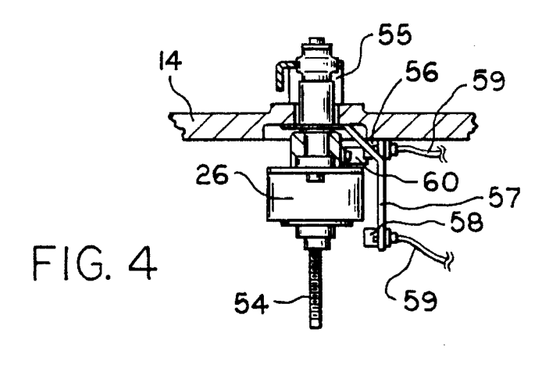
FIG. 4 is a side sectional view of an elevation motor and associated elevation limit detector of the present invention.
Figure 5:
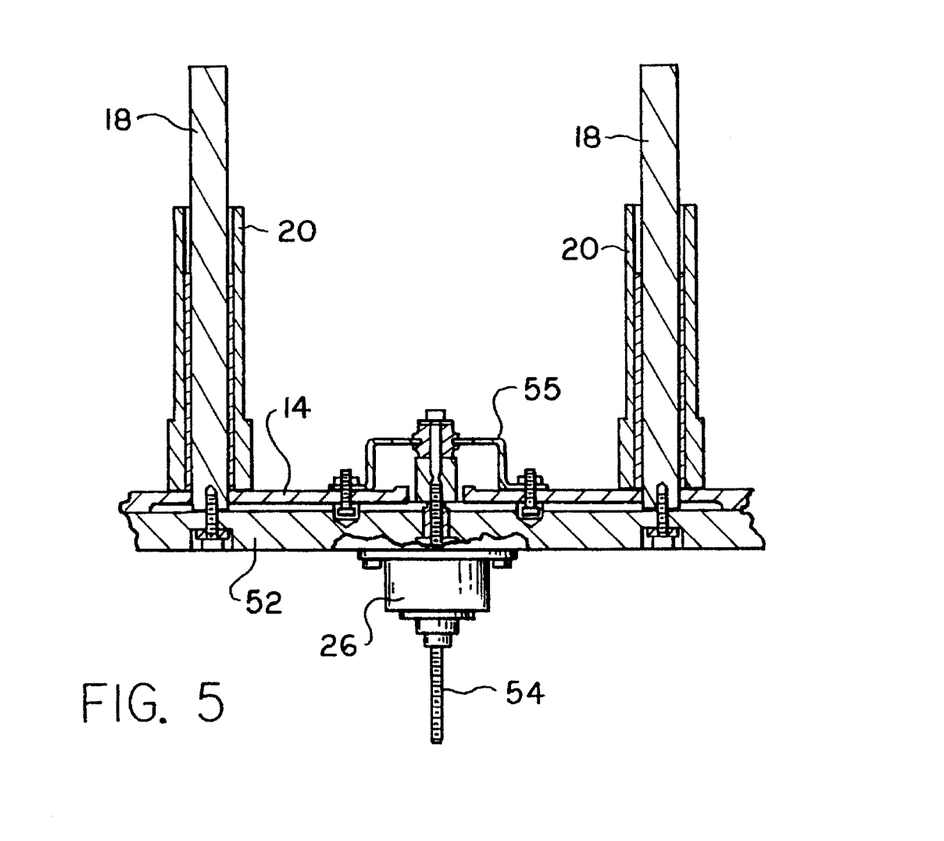
FIG. 5 is a sectional view taken generally along the line 5—5 in FIG. 2.

Referring now to FIGS. 2, 4, and 5, elevation motor 26 is fixed to a lower member 52 of support 16 and includes an internally threaded rotor (not shown) for mating with a threaded rod 54 having an upper portion fixed to carrier 14 by a mounting bracket 55 and a lower portion extending downwardly through carrier 14 and lower member 52. A suitable motor for use in practicing the present invention is a 12 Volt DC, 4.6 Watt bi-directional stepper motor No. 36343-12 available from Haydon Switch and Instrument, Inc. An upper limit switch 56 and a lower limit switch 58 are mounted on a brace 57 and connected to the motor control electronics by leads 59, and a tab 60 is fixed for travel with lower member 52 to interrupt light sensors on upper limit switch 56 upon reaching an uppermost travel limit and lower limit switch 58 upon reaching a lowermost travel limit, thereby causing the respective limit switch to send a signal to the motor control electronics to disable elevation motor 26 when either travel limit is reached. A preferred limit switch is optical transmissive switch model number HOA 1881-11 manufactured by Honeywell.

Figure 7:
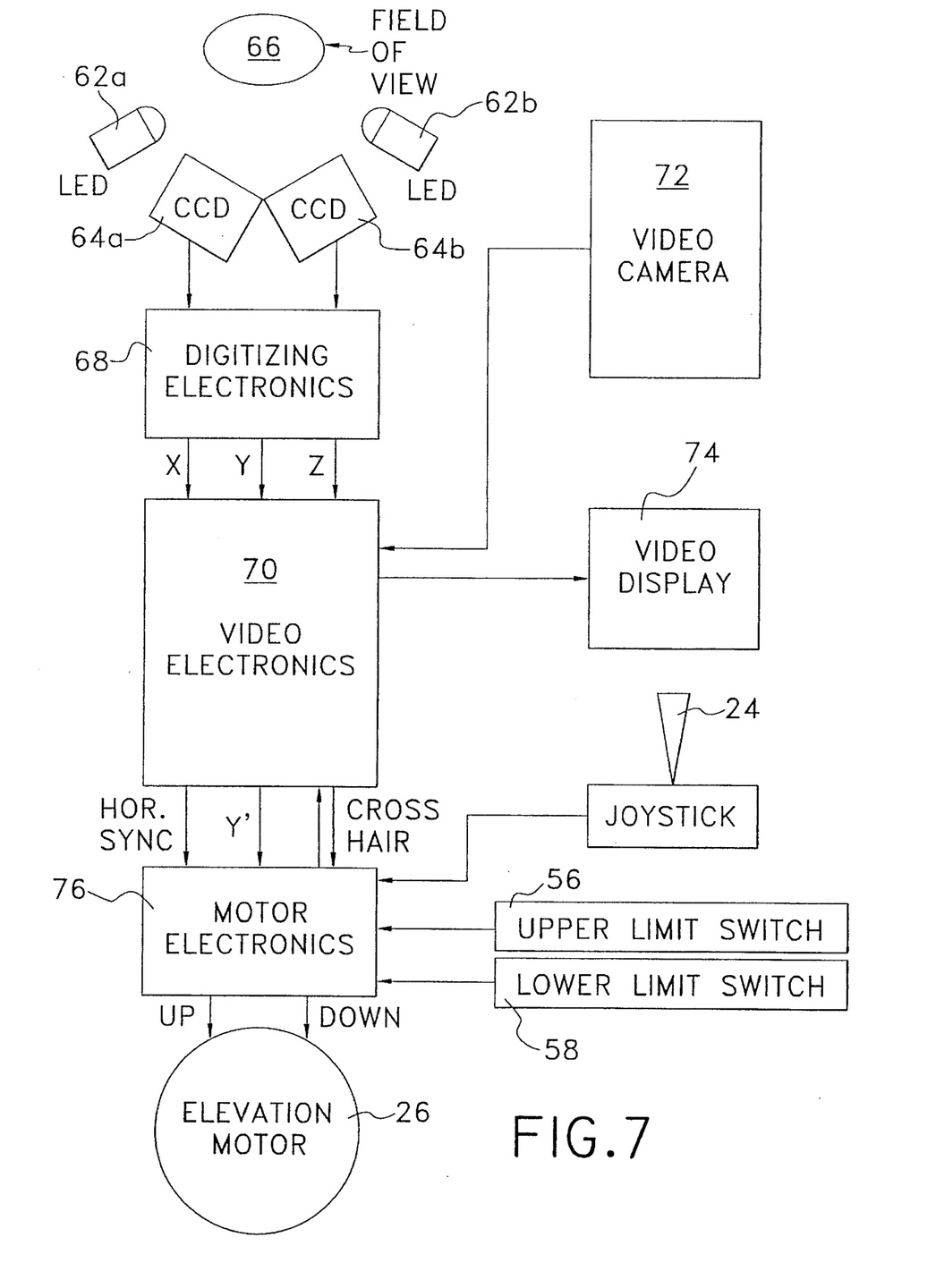
FIG. 7 is a block diagram of an ophthalmic instrument incorporating the present invention.

The block diagram of FIG. 7 illustrates generally the functional organization of electronic components in NCT 10. NCT 10 is equipped with an optical alignment system wherein optical means 22 includes a pair of LEDs 62a, 62b for illuminating an eye, and a pair of CCD arrays 64a, 64b arranged in a known manner to define a field of view 66. LEDs 62a, 62b and CCDs 64a, 64b cooperate to generate signal information indicative of the location of a patient's eye within field of view 66. This information is passed to digitizing electronics 68, which in turn provides a set of signals representing the X, Y, and Z distances of test axis 23 from the center of the eye to video electronics 70. Video electronics 70 also receives a macro video image signal of the eye from a video camera 72. Video electronics 70 delivers output to a video display 74 giving visual alignment instructions to an operator, such as orthogonal cross-hairs superimposed on the macro image of the eye. In addition, video electronics provides a vertical location signal Y' representing the Y location of the center of the eye relative to a chosen video display reference. A complete description of a preferred optical alignment system is provided in commonly owned U.S. Pat. No. 4,881,807 issued Nov. 21, 1989.

In accordance with the present invention, signal information is passed from video electronics 70 to motor control electronics 76. When the eye is outside field of view 66, joystick 24 connected to motor control electronics 76 provides the operator with means for manually positioning optical means 22 and test axis 23 with respect to the eye. However, when the eye comes into field of view 66, motor control electronics 76 uses information from video electronics 70 to override joystick 24 and automatically drive elevation motor 26 to vertically align test axis 23 with the center of the eye. As previously mentioned, upper limit switch 56 and lower limit switch 58 provide a signal to motor control electronics 76 to disable elevation motor 26 when either vertical travel limit has been reached.

Figure 8A:
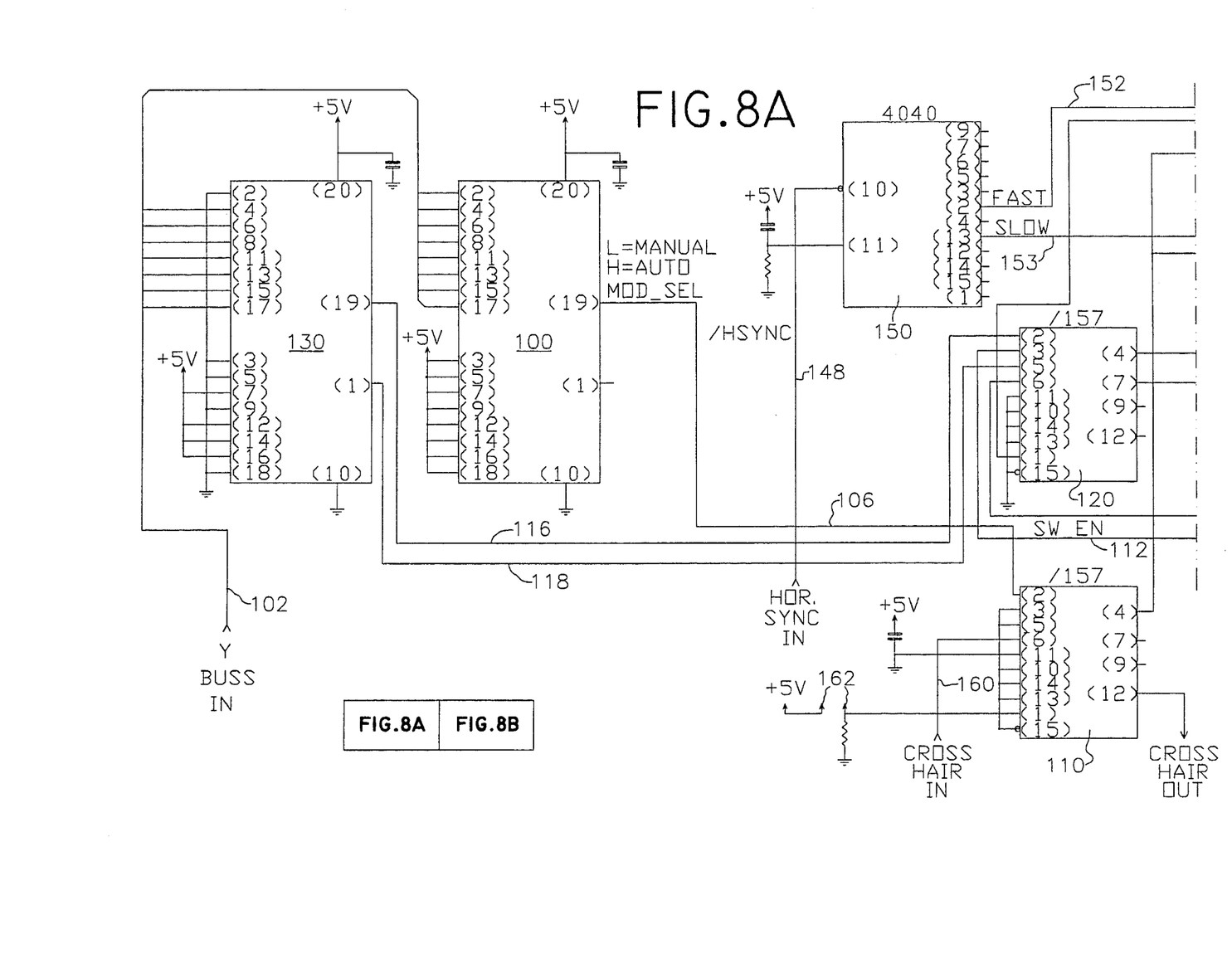
FIG. 8 is an electrical schematic diagram of the motor control electronics thereof.
Figure 8B:
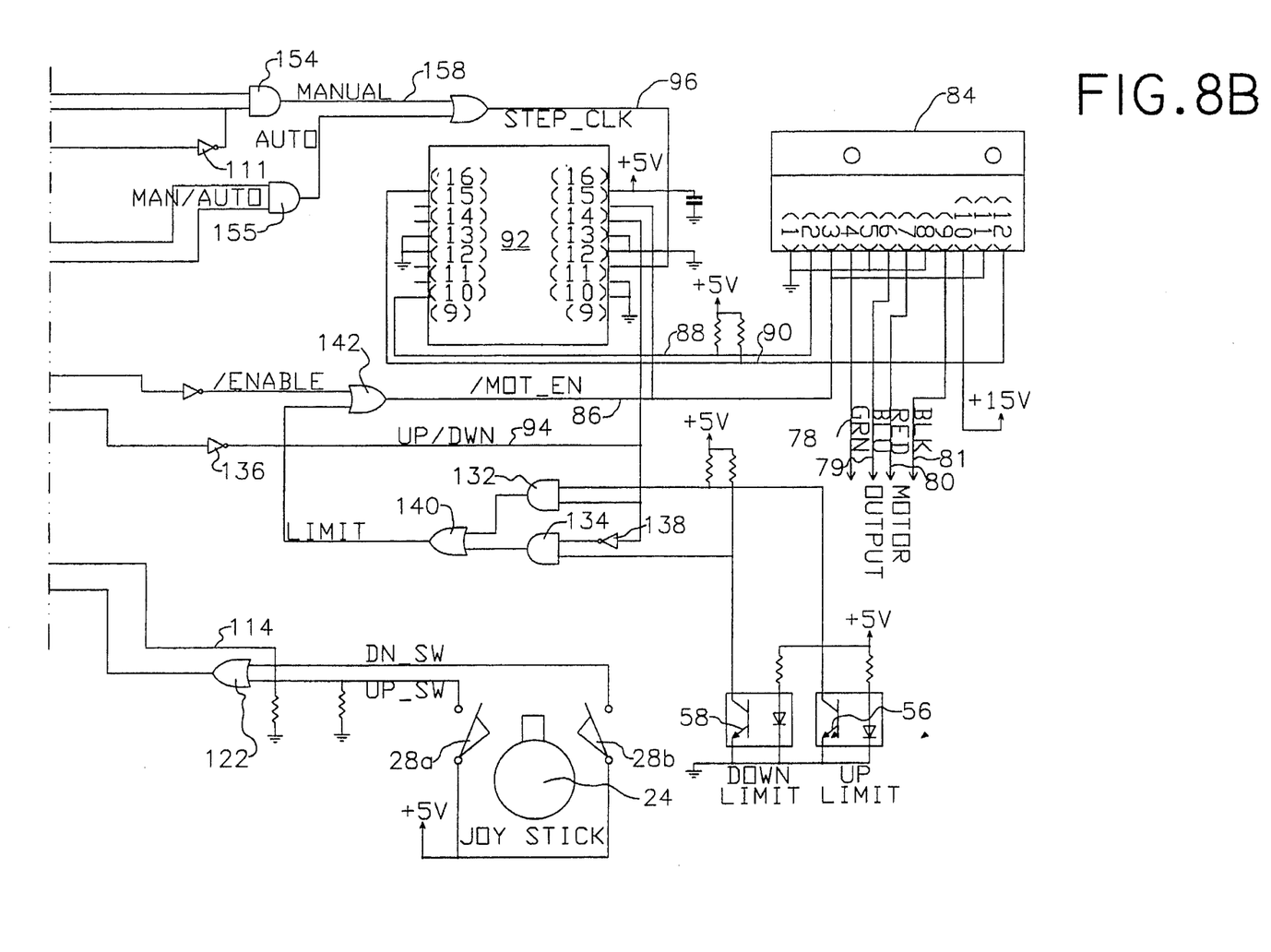

Referring now to FIG. 8, the motor control electronics incorporating the joystick override control of the present invention is represented schematically. Elevation motor 26 is connected to output lines 78–81 corresponding to pins 4, 6, 7 and 9, respectively, from a motor driver 84, which is preferably a dual full-bridge motor driver model number UDN2998W available from Allegro. Pins 3 and 11 of motor driver 84 are associated with motor enable input line 86. Motor driver 84 is responsive to a logical low motor enable signal from line 86 for enabling elevation motor 26, while a logical high motor enable signal will disable elevation motor 26. Motor driver 84 is further responsive to a pair of phase input signals carried over lines 88 and 90 connected to pins 2 and 12, respectively. Elevation motor 26 is enabled either manually, such as by joystick 24 engaging switch 28a or 28b, or automatically, where the eye comes within field of view 66 of optical means 22, to move test axis 23 vertically for alignment with the center of the eye.

Motor driver 84 is connected to a stepper-motor translator/driver 92, preferably model number UCN5804B manufactured by Allegro, for controlling the step speed and direction of rotation of elevation motor 26. Translator/driver 92 includes a motor enable input at pin 15 for receiving the motor enable signal carried by line 86, a direction input at pin 14 for receiving a direction signal carried by line 94, a step speed input at pin 11 for receiving a clock pulse signal carried by line 96, and a pair of outputs at pins 1 and 8 connected to phase input pins 2 and 12 of motor driver 84 by lines 88 and 90, respectively.

A first 8-bit comparator 100, preferably Texas Instruments model number SN74HC682, is connected to receive 8-bit vertical location signal Y' at pins 2, 4, 6, 8, 11, 13, 15, and 17 thereof transmitted by video electronics 70 over Y bus 102, and includes a mode selection output at pin 19 for transmitting a mode selection signal over line 104. First comparator 100 determines whether the vertical location signal received via Y bus 102 is equal to a null byte supplied to pins 3, 5, 7, 9, 12, 14, 16, and 18 thereof. When the eye is outside field of view 66, the vertical location signal is equal to a null byte, and the mode selection output signal is driven low for manual (joystick) control mode; conversely, when the eye is within field of view 66, the vertical location signal is other than a null byte, and the mode selection output signal is driven high for automatic control mode.

The mode selection signal is preferably fed via line 106 through a first logic means 110, to be described in detail below, and is subsequently inverted by an inverter 111 before being delivered to a second logic means 120, suitably a National Semiconductor model number MM74HC157 Quad 2-Input Multiplexer. Second logic means 120 includes a select input at pin 1 for receiving the mode selection signal and either connecting switches 28a, 28b to the motor drive means 84 and 92 where the received mode selection signal is high, or disconnecting the switches from the motor drive means and connecting video electronics 70 thereto for effecting automatic alignment where the received mode selection signal is low.

Second logic means 120 further includes a first motor enable input at pin 3 and a first motor direction input at pin 6 connected to switches 28a, 28b by lines 112 and 114, respectively, for manual motor control, and a second motor enable input at pin 2 and a second motor direction input at pin 5 connected to a second comparator 130 by lines 116 and 118, respectively, for automatic motor control. Up switch 28a and down switch 28b are each connected to OR gate 122 whose output is fed over line 112, such that when either switch is closed, the motor enable signal delivered to input pin 3 is driven high. Down switch 28b is directly connected by line 114 to input pin 6 to drive the direction signal high incident to closing of the down switch.

Second comparator 130 is connected to Y-bus 102 to receive vertical location signal Y' representing the Y location of the center of the eye relative to a chosen video display reference, and includes a motor enable output at pin 19 and a motor direction output at pin 1 connected to pins 2 and 5 of second logic means 120 by lines 116 and 118, respectively. Second comparator 130 compares the vertical location signal with a predetermined 8-bit signal supplied to pins 3, 5, 7, 9, 12, 14, 16 and 18 thereof representing an optimal Y location of test axis 23 relative to the aforementioned video display reference. If the vertical location signal Y' is less than the predetermined optimal location signal, then the eye center is below test axis 23 and the motor direction signal output from pin 1 is driven high for downward movement of the test axis. Conversely, where the vertical location signal is greater than the predetermined optimal location signal, the motor direction signal is driven low for upward movement of the test axis. Once test axis 23 has been moved by elevation motor 26 such that vertical location signal Y' equals the predetermined optimal location signal, automatic vertical alignment is achieved and the motor enable signal from pin 19 is driven low to disable elevation motor 26.

As described hereinabove, upper limit switch 56 and lower limit switch 58 are provided for disabling elevation motor 26 when test axis 23 reaches a predetermined upper travel limit or a predetermined lower travel limit, respectively. Upper limit switch 56 and lower limit switch 58 are connected as first inputs to AND gates 132 and 134, respectively. The direction signal output from pin 7 of second logic means 120 is inverted by an inverter 136 and fed as a second input to AND gate 132. An inverter 138 serves to provide an opposite direction signal as a second input to AND gate 134. The output signals from AND gates 132 and 134 are passed to an OR gate 140, whose output in turn is fed to an OR gate 142. The direction signal input to AND gate 132 during upward travel of elevation motor 26 is high, and the signal input to AND gate 132 from upper limit switch 56 is driven high incident to elevation motor 26 reaching its upper travel limit, thereby resulting in a high signal being delivered to OR gate 140 and subsequently to OR gate 142. Consequently, the motor enable signal leaving OR gate 142 is driven high to disable elevation motor 26. Lower limit switch 58 works in a similar manner via AND gate 134, with the direction signal input thereto being driven high during downward travel of elevation motor 26.

The clock pulse input delivered via line 96 to pin 11 of translator/driver 92 controls the step speed of elevation motor 26. When the motor drive means is under manual control, a fast clock pulse rate is supplied for correspondingly fast vertical movement of optical means 22; when the motor drive means is under the automatic override control, a relatively slower clock pulse rate is supplied for correspondingly slower vertical movement of optical means 22. Clock pulse timing originates with the delivery of a horizontal synchronization signal from video electronics 70 over line 148 to a binary counter/divider means 150, which may be a Harris CMOS Ripple-Carry Binary Counter/Divider model number CD4040B having a pulse input at pin 10 and a reset input at pin 11. The horizontal synchronization signal from video electronics 70 has a typical frequency of 15,750 Hertz, which is divided by 64 to produce a fast clock pulse rate output from pin 2, and divided by 256 to produce a slow clock pulse rate output from pin 13. The fast and slow clock pulse rates are delivered over lines 152 and 153 to AND gates 154 and 155, respectively. In addition to the fast clock pulse rate, AND gate 154 receives as input the mode selection signal originating from first comparator means 100 inverted by inverter 111. AND gate 155 receives as input the uninverted mode selection signal for evaluation with the slow clock pulse rate. The outputs from AND gates 154 and 155 are passed through OR gate 158. Consequently, where the uninverted mode selection signal is logical low for manual control mode, the slow clock pulse rate will be blocked at AND gate 155 and the fast clock pulse will be transmitted through AND gate 154 and OR gate 158 to line 96 for input to pin 11 of translator/driver 92. Where the uninverted mode selection signal is logical high for automatic mode, the slow clock pulse rate will be passed to translator/driver 92 in a similar but opposite manner.

First logic means 110 is suitably a National Semiconductor model number MM74HC157 Quad 2-Input Multiplexer identical to second logic means 120 and includes pins 2 and 4 for respective input and output of the mode selection signal transmitted by first comparator 100 over line 106, and pins 6 and 7 for respective input and output of a cross-hair signal delivered from video electronics 70 over line 160. First logic means 110 further includes a select input pin 1 preferably connected to an externally accessible lockout means 162 for driving the select input high, whereby the mode selection signal may be selectively bypassed to disconnect the automatic override control to provide exclusive manual control by joystick 24 and switches 28a, 28b with a cross-hair display. The provision of lockout means 162 enables a technician to perform initial calibration and alignment of NCT 10.

As may be appreciated from the above description, NCT 10 is significantly easier to operate than prior art ophthalmic instruments, particularly with respect to vertical positioning of test axis 23. To manually raise test axis 23, an operator merely rotates joystick 24 clockwise through a minimal angle until actuator 30 operatively engages switch bumper 50a on switch 28a, thereby causing the internally threaded rotor of elevation motor 26 to rotate in a first direction, forcing the elevation motor and support 16 attached thereto to travel upward along threaded rod 54. Depending on the type of switch 28a, upward travel of optical means 22 may be halted either by returning the joystick to its original reference position away from engagement with switch bumper 50a, or by repeating a "rotate and return" cycle used to commence upward motion. Manual downward positioning of test axis 23 is commenced in a similar but opposite manner by rotating joystick 24 counterclockwise from its reference position until actuator 30 operatively engages switch bumper 50b.

Once the eye comes within field of view 66, the joystick override control of the present invention effects automatic vertical alignment of test axis 23 with the center of the eye.

While the present invention is directed to motorized movement in opposite vertical (Y) directions, motorized movement in all three dimensions has been described previously, for instance in aforementioned U.S. Pat. No. 4,881,807 at column 6, lines 31–44 and FIG. 7, and thus it is contemplated to provide similar motorized movement in the horizontal X and Z directions in combination with manual and automatic override control therefor.

What is claimed is:

1. An ophthalmic instrument alignment override comprising: a test axis passing through said instrument, motor drive means for moving said axis vertically, a first switch to activate said drive means in one direction, a second switch to activate said drive means in the other direction, manual means for selectively engaging said first or second switches to provide manual control of said drive means, optical means having a field of view and means for detecting the position of an eye, said optical means including signal means to generate a signal having a value representing a vertical location of the eye relative to said axis when the eye is within said field of view, and comparator means to determine when said signal means generates said signal and shift control of said drive means from said first and second switches to said signal, whereby said optical means is in exclusive control of said drive means if the eye is within said field of view.

2. The override according to claim 1, wherein said manual means is a joystick.

3. The override according to claim 2, wherein an actuator protrudes from said joystick for selective engagement of said first or second switch when said joystick is rotated.

4. The override according to claim 1, wherein said signal is a digital signal.

5. The override according to claim 4, wherein said drive means includes a stepper motor and a stepper motor driver having a step speed input responsive to a clock pulse.

6. The override according to claim 5, wherein said comparator means further incudes means to provide one clock pulse rate for manual control of said drive means and another clock pulse rate when said optical means is in exclusive control of said drive means.

7. The override according to claim 6, wherein said one clock pulse rate is faster than said another clock pulse rate.

8. The override according to claim 6, wherein said comparator means further includes lockout means to temporarily prevent exclusive control by said optical means.

9. In a non-contact tonometer having an optical means including a pair of light sources for illuminating an eye, a pair of X-Y area detectors having a field of view, and a test axis, manual means for moving said optical means relative to said eye, digitizing electronics for providing an X signal, a Y signal, and a Z signal when said eye is within said field of view, said X and Y signals representing the respective X and Y distances of said test axis from the center of said eye and said Z signal representing the distance of said optical means from said eye along said test axis;

camera means for providing a recorded image of said eye, video electronics for processing said X, Y, and Z signals and providing a television signal representing said recorded image and a symbol, said television signal including a vertical location signal representing the Y location of the center of said eye relative to a video display reference; and a television monitor for displaying said recorded image and said symbol;

the improvement comprising:

a motor drive means for moving said optical means vertically;

a first switch and a second switch selectively disconnectable from said drive means for enabling said drive means and controlling the direction of vertical movement;

a first comparator means to evaluate said vertical location signal and provide a first comparator output indicating if said eye is within said field of view;

a second comparator means to evaluate said vertical location signal and provide a second comparator output indicating the vertical direction to move said optical means for alignment of said test axis with the center of said eye; and logic means to evaluate said first comparator output and disconnect said first and second switches if said eye is within said field of view, and to evaluate said second comparator output and enable said drive means and select the vertical direction to move said optical means.

* * * * *